United States Patent [19]

Edwards

[11] Patent Number: 4,665,236

[45] Date of Patent: May 12, 1987

[54] ALKOXYLATION PROCESS USING BIMETALLIC OXO CATALYST

[75] Inventor: Charles L. Edwards, Houston, Tex.

[73] Assignee: Shell Oil Company, Houston, Tex.

[21] Appl. No.: 847,980

[22] Filed: Apr. 3, 1986

Related U.S. Application Data

[63] Continuation-in-part of Ser. No. 666,062, Oct. 29, 1984, abandoned.

[51] Int. Cl.$^4$ .............................................. C07C 41/03
[52] U.S. Cl. ...................................... 568/618; 568/39; 568/45; 568/608; 568/620; 568/622; 568/678; 568/679; 560/263; 560/265; 560/200; 560/240; 569/505; 569/399; 569/475
[58] Field of Search ............... 568/618, 620, 622, 678, 568/679

[56] References Cited

U.S. PATENT DOCUMENTS

| | | | |
|---|---|---|---|
| 3,432,445 | 3/1969 | Osgan et al. | 528/412 |
| 3,671,466 | 6/1972 | Shikata et al. | 568/606 |
| 4,112,231 | 9/1978 | Weibull et al. | |
| 4,483,941 | 11/1984 | Yang | 568/618 |

OTHER PUBLICATIONS

Teyssie et al., Chem. Tech., Mar. 1977, pp. 192-194.

*Primary Examiner*—Howard T. Mars

[57] ABSTRACT

Alkylene oxide adducts of organic compounds having an active hydrogen are prepared by a process in which an active hydrogen reactant and an alkylene oxide reactant are reacted in the presence of a catalytically effective amount of one or more bimetallic oxo compounds of the formula $(RO)_nM-O-M'-O-M(OR)_n$, wherein each R is (independently) an optionally-substituted organic moiety, M' is a divalent metal selected from the elements of Groups VIII, Ib, IIb, IIIb, and IVb of the Periodic Table, each M is (independently) a trivalent or tetravalent metal, and each n is 2 if the adjacent M is trivalent of 3 if the adjacent M is tetravalent. The products are useful, for instance, as nonionic surfactants in detergent formulations. In certain preferred embodiments, the process yields a product having a very desirable distribution of alkylene oxide adducts.

19 Claims, No Drawings

ALKOXYLATION PROCESS USING BIMETALLIC OXO CATALYST

This is a continuation-in-part of Ser. No. 666,062 filed Oct. 29, 1984 now abandoned.

BACKGROUND OF THE INVENTION

This invention relates to the preparation of reaction products of alkylene oxides with alcohols and other organic compounds having an active hydrogen. More particularly, this invention is directed to a process for such preparation employing a particular bimetallic compound as catalyst.

A large variety of products useful, for instance, as surfactants, solvents, and chemical intermediates, are prepared by the addition reaction (alkoxylation reaction) of alkylene oxides with organic compounds having one or more active hydrogen atoms. As an example, particular mention may be made of the alcohol ethoxylates and alky-substituted phenol ethoxylates prepared by the reaction of ethylene oxide with aliphatic alcohols or substituted phenols of about 8 to 20 carbon atoms, which ethoxylates are common nonionic detergent components of commercial cleaning formulations for use in industry and in the home. An illustration of the preparation of such an aliphatic alcohol ethoxylate (represented by formula III below) by addition of a number (p) of ethylene oxide molecules (formula II) to a single alcohol molecule (formula I) is presented by the equation

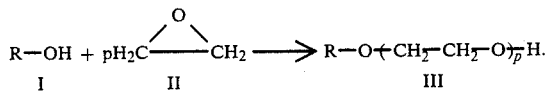

Alkylene oxide addition reactions are known to be promoted by contact with a catalyst, conventionally a catalyst of either acidic or basic character. Recognized in the art as suitable basic catalysts are the soluble basic salts of the alkali metals of Group I of the Periodic Table, e.g., sodium, potassium, rubidium, and cesium, and the soluble basic salts of certain of the alkaline earth metals of Group II of the Periodic Table, e.g., calcium, strontium, and barium. Conventional acidic alkoxylation catalysts include, broadly, the Lewis acid or Friedel-Crafts catalysts. Specific examples of these catalysts are the fluorides, chlorides, and bromides of boron, antimony, tungsten, iron, nickel, zinc, tin, aluminum, titanium and molybdenum. The use of complexes of such halides with, for example, alcohols, ethers, carboxylic acids, and amines have also been reported. Still other examples of known acidic alkoxylation catalyts are sulfuric and phosphoric acids; the perchlorates of magnesium, calcium, manganese, nickel and zinc; metals oxalates, sulfates, phosphates, carboxylates and acetates; alkali metal fluoroborates, zinc titanate; and metal salts of benzene sulfonic acid.

In one important aspect, the present invention relates to an alkoxylation reaction catalyzed by certain bimetallic oxo compounds. Such substances have been known in the chemical arts. Description of these and related compounds are described, for instance, in U.S. Pat. No. 3,432,445, Belgian Pat. No. 680,456, U.S. Pat. Nos. 3,607,785, 4,281,087, 4,419,482, and U.S Pat. No. 3,576,762, and in the publication of Ph. Teyssie et al entitled "Catalysis with Soluble M—O—M'—O—M Bimetallic Oxides (*Chemtech.*, Mar. 1977, p. 193). The bimetallic oxo compounds have not, however, been recognized as useful in promoting alkoxylation reactions.

In other aspects, the invention further involves the discovery of a process for the production of alkylene oxide adducts (alkoxylates) characterized by a narrow alkylene oxide adduct distribution. Alkylene oxide addition reactions are known to produce a product mixture of various alkoxylate molecules having a variety of alkylene oxide adducts, (oxyalkylene adducts), e.g., having different values for the adduct number p in formula III above. The adduct number is a factor which in many respects controls the properties of the alkoxylate molecule, and substantial effort is often devoted to tailoring the adduct number distribution of a given product mixture to its intended service. In certain preferred aspects, the present invention is a process characterized by enhanced selectivity for the preparation of alkoxylate mixtures in which a relatively large proportion of the alkoxylate molecules have a number (p) of alkylene oxide adducts that is within a relatively narrow range of values. It is known that alkoxylate products having such a narrow range distribution are preferred for use in detergent formulations (Great Britain Pat. No. 1,462,134; Derwent Publications Research Disclosure No. 194,010). Narrow-range alkoxylates are also known to be particularly valuable as chemical intermediates in the synthesis of certain carboxyalkylated alkyl polyethers (U.S. Pat. No. 4,098,818) and of certain alkyl ether sulfates (Great Britain Pat. No. 1,553,561).

Attempts made in the prior art to produce alkoxylates having a more narrow-range distribution of alkylene oxide adducts have centered upon processes for the preparation of alcohol alkoxylates, and most particularly upon the preparation of ethylene oxide adducts of higher ($C_8$ to $C_{20}$) aliphatic primary alcohols. The common conventional basic catalysts, i.e., compounds of the alkali metals, are known to be responsible for the production of alcohol ethoxylates having a relatively broad distribution. Conventional acid-catalyzed alkoxylation catalysts have long been recognized to produce alcohol ethoxylate products having a narrow distribution of alkylene oxide adducts. However, acid catalysis is known to have substantial disadvantage in several respects. For instance, the acids are often unstable, with limited life and effectiveness as catalysts in the ethoxylation mixture. Both the catalysts themselves and their decomposition products catalyze side reactions producing relatively large amounts of polyethylene glycols, and also react directly with the components of the alkoxylation mixture to yield organic derivatives of the acids. Overall, use of acid ethoxylation catalysts is known to result in relatively poor quality products.

A great deal of attention has recently been given in the art to processes which utilize basic compounds of the alkaline earth metals as catalysts for the preparation of alcohol alkoxylate products having a relatively narrow-range distribution. For instance, it has recently been reported (U.S. Pat. Nos. 4,210,764, 4,223,164, 4,239,917, 4,453,022, 4,453,023, 4,302,613, and 4,375,564 and the published European patent applications Ser. Nos. 0026544, 0026546, 0026547, 0085167 and 0092256) that alkoxylation promoted by basic barium, strontium, calcium and magnesium compounds, either alone or with specified co-catalysts, yields an alkoxylate having a distribution which is more narrow or peaked than that of the product of an alkoxylation promoted by basic compounds of the Group I metals. Such products are still, however, considered to be less than optimal from the standpoint of overall product quality, requirements for catalyst removal, and/or narrowness of product distribution.

Other recent disclosures of related alkoxylation processes include U.S. Pat. No 4,456,697, which reports the use of a catalyst combining HF and a metal or mixed metal alkoxide of the formula $M(OC_nH_{2n+1})q$ wherein M is selected from the group consisting of aluminum, gallium, indium, thallium, zirconium, hafnium, and titanium as well as U.S. Pat. No. 4,375,564 which describes catalysts combining a magnesium compound with a compound of an element selected from the group consisting of aluminum, boron, zinc, titanium, silicon, molybdenum, vanadium, gallium, germanium, yttrium, zirconium, niobium, cadmium, indium, tin, antimony, tungsten, hafnium, tantalum, thallium, lead, and bismuth.

SUMMARY OF THE INVENTION

It has now been found that certain bimetallic oxo compounds are useful as catalysts for the addition reaction of alkylene oxides with alcohols and other organic compounds having one or more active hydrogen atoms.

Accordingly, in the broad sense, the invention is a process for the preparation of alkoxylates of active hydrogen containing compounds, which comprises contacting an alkylene oxide reactant (e.g., ethylene oxide, propylene oxide, etc.) with an active hydrogen reactant (e.g., one or more alcohols, phenols, thiols, amines, polyols, or carboxylic acids) in the presence of a catalyst comprising one or more bimetallic oxo compounds of the formula

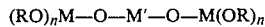

$$(RO)_nM-O-M'-O-M(OR)_n$$

wherein R (individually in each occurrence) represents an optionally-substituted organic moiety, M' represents a divalent metal selected from elements of Groups VIII, Ib, IIb, IIIb, and IVb of the Periodic Table, M represents (individually in each occurrence) either a trivalent metal or a tetravalent metal, and n is 2 if the adjacent M is a trivalent metal or 3 if the adjacent M is a tetravalent metal.

It has further been found that the use of such bimetallic oxo compounds as alkoxylation catalysts provides a process for the preparation of an alkoxylate product, particularly an alkanol ethoxylate product, having an exceptionally narrow-range alkylene oxide adduct distribution. This product is of high quality (relatively free of by-products) and is characterized by a distribution which is notably more narrow or peaked than that of products of conventional alkoxylation reactions catalyzed by basic compounds of either the alkali metals or the alkaline earth metals.

BRIEF DESCRIPTION OF THE DRAWING

The attached drawing represents, in its one FIGURE, a representative plot of the distribution of alkylene oxide adducts in products prepared by reaction of ethylene oxide with $C_{12}$ and $C_{13}$ primary linear aliphatic alcohols in the presence of each of three different catalysts. The curve designated A represents the typical distribution of a product prepared using a conventional basic alkali metal alkoxylation catalyst, specifically KOH; curve B represents the typical distribution of a product prepared using a conventional basic alkaline earth metal alkoxylation catalyst, specifically barium hydroxide; and curve C represents the distribution of a product prepared under practice in accordance with the invention. In each case, the alkoxylate product exhibits a peak in its distribution at an adduct number in the range from about 1.5 to 1.9.

The drawing will be further described in the Examples of the invention which follow.

DESCRIPTION OF THE PREFERRED EMBODIMENTS

The present invention centers upon discoveries associated with the use in an alkoxylation process of a certain class of catalysts. Apart from the use of such catalysts, the process of the invention is, as a general rule, suitably conducted using such reactants and practicing under such processing procedures and reaction conditions as are known to the art for alkoxylation reactions. Certain preferences may, however, be expressed for particular reactants, procedures and conditions.

Thus, for instance, the invention is generally applicable to processes utilizing any alkylene oxide (epoxide) reactant containing one or more alkylene oxides having from two to about 20 carbon atoms. Specific examples of alkylene oxides suitable for use in the alkoxylation of active hydrogen containing compounds are well known in the art. Preference generally exists for the use of the lower, e.g., $C_2$ to $C_8$ alkylene oxides and for the use of the vicinal alkylene oxides. From the standpoint of commercial interest, specific mention may be made of the $C_2$ to $C_4$ vicinal alkylene oxides, including ethylene oxide, propylene oxide, and the 1,2- and 2,3-butylene oxides. Particularly preferred are ethylene oxide and propylene oxide, while use of ethylene oxide is considered most preferred. Mixtures of alkylene oxides are suitable, in which case the product of the invention will be a mixed alkoxylate.

Likewise, the active hydrogen reactants suitably utilized in the process of the invention include those known in the art for reaction with alkylene oxides and conversion to alkoxylate products. The suitable classes of active hydrogen reactants include, but are not necessarily limited to alcohols, phenols, thiols (mercaptans), amines, polyols, carboxylic acids, and mixtures thereof.

Among the suitable carboxylic acids, particular mention may be made of the mono- and dicarboxylic acids, both aliphatic (saturated and unsaturated) and aromatic. Specific examples include acetic acid, propionic acid, butyric acid, valeric acid, caproic acid, lauric acid, myristic acid, palmitic acid, steric acid, oleic acid, rosin acids, tall oil acids, terephthalic acid, benzoic acid, phenylacetic acid, toluic acid, acrylic acid, methacrylic acid, cotonic acid, maleic acid, and the like.

Among the suitable amines, particular mention may be made of primary, secondary and tertiary alkylamines and of alkylamines containing both amino and hydroxyl groups, e.g., N,N-di(n-butyl)-ethanolamine and tripropanolamine.

Among the suitable thiols, particular mention may be made of primary, secondary and tertiary alkane thiols having from 1 to about 30 carbon atoms, particularly those having from about 8 to 20 carbon atoms. Specific examples of suitable tertiary thiols are those having a highly branched carbon chain which are derived via hydrosulfurization of the products of the oligomerization of lower olefins, particularly those dimers, trimers, and tetramers and pentamers of propylene and the butylenes. Secondary thiols are exemplified by the lower alkane thiols, such as 2-propanethiol, 2-butanethiol, and 3-pentanethiols, as well as by the products of the hydrosulfurization of the substantially linear oligomers of ethylene as are produced by the Oxo process. Representative, but by no means limiting, examples of thiols derived from ethylene oligomers include the linear carbon chain products, such as 2-decanethiol, 3-decanethiol, 4-decanethiol, 5-decanethiol, 3-dodecanethiol, 5-dodecanethiol, 2-hexadecanethiol, 5-hexadecanethiol, and 8-octadencanethiol, and the branched carbon chain products, such as 2-methyl-4-tridecanethiol. Primary thiols are typically prepared from terminal olefins by hydrosulfurization under free-radical conditions and include, for example, 1-butanethiol, 1-hexanethiol, 1-dodecanethiol, 1-tetradecanethiol and 2-methyl-1-tridecanethiol.

Among the polyols, particular mention may be made of those having from 2 to about six hydroxyl groups. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, and tripropylene glycol, glycerine, sorbitol, and the like.

The alcohols and phenols are today the principal reactants in commercial alkoxylate production and are preferred classes of active hydrogen reactants for purposes of the invention. Among the phenols, particular mention may be made of phenol and of alkyl-substituted phenols wherein each alkyl substituent has from one to about 30 (preferably from one to about 20) carbon atoms, for example, p-methylphenol, p-ethylphenol, p-hexylphenol, p-decylphenol, didecyl phenol and the like.

Acyclic aliphatic alcohols form a most preferred class of reactants. In this regard, it is found that the aliphatic alcohols benefit to a relatively great degree from the capabilities of the invention for the preparation of alkoxylates having narrow-range or peaked alkylene oxide adduct distributions. This is particularly true for the primary mono-hydric aliphatic alcohols, although secondary and tertiary alcohols as well as polyhydric alcohols are also very suitably utilized in the process of the invention. Preference can also be expressed, for reason of both process performance and commercial value of the product, for aliphatic alcohols having from one to about 30 carbon atoms, with $C_6$ to $C_{24}$ alcohols considered more preferred and $C_8$ to $C_{20}$ alcohols considered most preferred. As a general rule, the aliphatic alcohols may be of branched or straight chain structure, although preference further exists for alcohol reactants in which greater than about 50 percent, more preferably greater than about 60 percent and most preferably greater than about 70 percent of the molecules are of linear (straight-chain) carbon structure.

Specific examples of primary straight-chain monohydric aliphatic alcohols include ethanol, hexanol, octanol, dodecanol, pentadecanol, octadecanol and eiscosanol. Specific examples of branched chain or secondary alcohols include isopropanol, isoheptanol, 3-heptanol, isodecanol, 2-methyl-1-nonanol, 2-methyl-1-undecanol, 4-tetradecanol, and 4-hexadecanol.

Mixtures of active hydrogen reactants in general and mixtures of alcohols in particular are suitable for purposes of the invention and are often preferred for reasons of their commercial availability. Mixtures of higher (e.g., $C_8$ to $C_{20}$) monohydric acyclic aliphatic alcohols are known to be commercially prepared, for instance, by hydroformylation of olefins or by reduction of naturally occurring fatty esters. Specific examples of commercially available alkanol mixtures in the $C_9$ to $C_{18}$ range are the NEODOL detergent alcohols, trademark of and manufactured by Shell Chemical Company, e.g., the products identified as NEODOL 91 alcohols (predominantly in the $C_9$ to $C_{11}$ range), NEODOL 23 alcohols, (predominantly $C_{12}$ and $C_{13}$ alcohols), NEODOL 25 alcohols (predominantly $C_{12}$ to $C_{15}$), and NEODOL 45 alcohols (predominantly $C_{14}$ and $C_{15}$).

Further general and specific illustrations of suitable alkoxylation process reactants, both the alkylene oxide reactants and the active hydrogen reactants, are provided by the above-referenced patents and published patent applications, the relevant teachings of which are incorporated herein for that purpose.

For purposes of the invention, the alkylene oxide reactant and the active hydrogen reactant are necessarily contacted in the presence of the specified bimetallic oxo catalyst. Such materials are known to the art and are conventionally represented by the formula $$(RO)_nM\text{—}O\text{—}M'\text{—}O\text{—}M(OR)_n.$$

M in the above formula represents (individually in each occurrence) either a trivalent metal or a tetravalent metal. Preferably, each M is independently selected from the group consisting of aluminum, titanium, boron, vanadium, scandium, germanium, yttrium, zirconium, tin, lanthanum and other members of the lanthanide series, hafnium, tantalum tungsten, palladium, and antimony. More preferably, each M is selected from the group consisting of aluminum, titanium, boron and vanadium, and most preferably each M is either aluminum or titanium.

M' in the above formula represents a divalent metal selected from those divalent metals of the Groups VIII, Ib, IIb, IIIb and IVb of the Periodic Table (i.e., the elements of atomic number 26-32, 44-50, and 76-82). M' is preferably selected from the group consisting of cobalt, nickel, copper, zinc, rhodium, palladium, silver, cadium, indium, tin, iridium, and platinum, and is more preferably selected from the group consisting of zinc, nickel, and cobalt. Most preferred as the M' metal are zinc and cobalt.

The R substituents in the above formula individually and independently represent any organic or substituted organic group, preferably a hydrocarbyl group and more preferably an alkyl group. The carbon numbers of the R substituents are not critical aspects of the invention, although preference may be expressed for R substituents each having from one to about 30 carbon atoms, most particularly from one to about 20 carbon atoms. Catalysts with lower alkyl (e.g., $C_1$ to $C_6$) R groups are most easily prepared and are very suitable for use in the invention. The use of catalysts having R substituents with carbon numbers in these ranges facilitates a homogeneous reaction mixture in which the catalyst is soluble in the active hydrogen containing reactant. It is not necessary, however, that the reaction involve homogeneous catalysis for purposes of the invention. In this regard one or more of the R substituents may suitably be of higher carbon number and/or the catalyst may be supported on a solid carrier, for example, silica, alumina, or a silica/alumina mixture, to produce a heterogeneous catalyst.

The subscripts n in the formula designate the number of OR groups bound to each M. If the adjacent M atom is trivalent n is 2, and if the adjacent M atom is tetravalent n is 3. It is to be emphasized that in any one bimetallic oxo molecule the two M atoms may be different, for example, one a trivalent metal and the other a different trivalent metal or a tetravalent metal. Likewise, the several R substituents in any one molecule may be the same or different organic radicals.

Methods for the preparation of bimetallic oxo compounds suitable for use in the invention are described in the aforementioned U.S. Pat. Nos. 3,432,445, 3,607,785, 4,281,087, and publication Chemtech, Mar. 1977, p. 193, the relevant teachings of which patents and publication are incorporated herein by this reference. A very convenient method for preparation of such a compound in which R represents an alkyl radical involves the reaction of two mols of trivalent and/or tetravalent metal (M) alkoxide with one mol of the acetate of a divalent metal (M'), for instance, at elevated temperature (e.g, 200° C.) and in the presence of a solvent (e.g., tetralin):

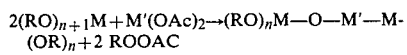

$$2(RO)_{n+1}M + M'(OAc)_2 \rightarrow (RO)_nM-O-M'-M-(OR)_{n+2} ROOAC$$

If desired, the bimetallic oxo compounds may be prepared with one set of R groups and then one or more different R group(s) substituted into the molecule by alcoholysis reaction.

The bimetallic oxo compound is present in the reaction mixture in a catalytically effective amount, typically at least about 0.01%w (percent by weight), based on the active hydrogen reactant. Although catalyst quantity is not narrowly critical, preference may be expressed for use of the catalyst in amount of at least about 0.1%w, while an amount between about 0.2 and 1.0%w is considered most preferred. Substantially greater quantities of bimetallic oxo catalyst, e.g., 10 or 20%w, are very suitable and may be preferred for applications involving heterogeneous catalysts.

In terms of processing procedures, the alkoxylation reaction in the invention may be conducted in a conventional manner. The active hydrogen reactant and the bimetallic oxo compound are very conveniently introduced into a reaction zone, followed by addition of that quantity of the alkylene oxide reactant necessary to produce an alkoxylate product of the desired mean or average adduct number, e.g., typically from less than one to about 30. In general terms, suitable and preferred process temperatures and pressures for reactions utilizing the bimetallic oxo catalysts are the same as in conventional alkoxylation reactions, between the same reactants, employing conventional catalysts. A temperature of at least about 60° C., particularly at least about 100° C., is typically necessary for a significant rate of reaction, while a temperature less than about 250° C., particularly less than about 200° C., and most particularly less than about 170° C., is typically necessary to minimize degradation of the product. Superatmospheric pressures are preferred for processes involving the lower (particularly $C_2$ to $C_4$) alkylene oxide reactants. While these procedures describe a batch mode of operation, the invention is equally applicable to a continuous process.

When the preferred $C_6$ to $C_{24}$ alkanols or the preferred alkyl-substituted phenols and the preferred $C_2$ to $C_4$ vicinal alkylene oxides are applied as reactants in the process of the invention, the alkoxylation reaction is preferably carried out at a temperature in the range from about 130° to 200° C., while a temperature between about 150° 190° C. is still more preferred. Considered most preferred is a reaction temperature in the range from about 165° to 175° C. A total pressure in the range from about 10 to 150 psig is usually preferred for the reaction between such higher alkanols or substituted phenols and lower alkylene oxides. The alkanol or phenol reactant is generally a liquid and the alkylene oxide reactant is generally a vapor for such reactions. Alkoxylation is the suitably conducted by introducing gaseous alkylene oxide into a pressure reaction zone containing the liquid alkanol. Catalyst is very conveniently in solution in, or otherwise mixed with, the alkanol. For considerations of process safety, the partial pressure of the lower alkylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater alkylene oxide concentration, greater total pressure and greater partial pressure of alkylene oxide if suitable precautions, known to the art, are taken to manage the risks of explosion. A total pressure of between about 40 and 110 psig, with an alkylene oxide partial pressure between about 15 and 60 psig, is particularly preferred, while a total pressure of between about 50 and 90 psig, with an alkylene oxide partial pressure between about 20 and 50 psig, is considered more preferred.

The alkoxylate prepared in the process of the invention is typically a product of very acceptable quality, having a relatively low content of polyalkylene glycols and other by-products. Unlike the products of typical acid or base catalyzed reactions of the prior art, the product of the invention is of essentially neutral pH. The bimetallic oxo compounds do not impart significant acidic or basic character to the reactants or to the product. Accordingly, it is not necessary, as in conventional practice, to neutralize the alkoxylate product by addition of base or acid. In this regard, the neutral pH of the process is considered to be a further desirable feature of the invention from the standpoint of product quality.

The high quality of the product, particularly in terms of the high selectivity of the process to the preparation of the desired adducts, is considered to be a surprising aspect of the invention, in view of recognition in the art of the use of like bimetallic oxo catalysts to promote the polymerization of alkylene oxides. In the aforementioned publication of Teyssie et al in Chemtech, Mar., 1977, p. 192, it is reported, for instance, that bimetallic oxo catalysts promote the polymerization of alkylene oxides, even when the reaction mixture contains active hydrogen compounds such as alcohols. Alkylene oxide polymers, also known as polyalkylene glycols, are generally known to be the major undesirable by-products of alkoxylation processes. For this reason, it is not predictable that catalysts recognized for their activity in promoting polymerization of alkylene oxides would be suitable for use as alkoxylation catalysts.

The production of an alkylene oxide polymer upon contact of an alkylene oxide, a bimetallic oxo catalyst and an alcohol, as described in the cited publication of Teyssie et al, is considered to be attributable to the presence in the reaction mixture of a liquid solvent, e.g., a saturated hydrocarbon solvent such as n-heptane. It is not intended that the present invention be carried out in the presence of any such added material, acting as a liquid reaction solvent, which has any meaningful influence upon the reactivity of the alkylene oxide and active hydrogen reactants, in the presence of the bimetallic oxo catalyst.

Thus, for example, if the process is one involving the contact and reaction in a reaction zone comprising a vapor phase lower alkylene oxide reactant (i.e., a $C_2$ to $C_4$ vicinal alkylene oxide, particularly ethylene oxide, propylene oxide, or mixtures thereof) and a liquid phase higher (e.g., $C_6$ to $C_{24}$) acyclic aliphatic alcohol, the liquid phase is preferably essentially solvent-free, that is essentially free of a hydrocarbon or other added solvent which adversely influences the alkoxylation reaction or promotes any other competing reaction involving the alkylene oxide and/or the alcohol. More preferably, the liquid phase of such a reaction zone is essentially solvent-free and consists essentially of the alcohol, the catalyst, and (once the alkoxylation reaction has commenced) the alkoxylate product. Most preferably, the liquid phase in such a reaction zone is solvent-free and consists of the reactants, the catalyst, and the product (together with minor amounts of impurities which may inherently be present in the alcohol and catalyst, minor amounts of inert gas components in solution in the alcohol and alkoxylate, and minor amounts of by-products (e.g., polyalkylene glycols) which are produced along with the desired alkoxylate).

The following Examples and Comparative Experiments are provided to further illustrate certain specific aspects of the invention but are not intended to limit its broader scope.

EXAMPLE 1

An alkoxylation process in accordance with the invention was carried out using a bimetallic (zinc and aluminum) oxo catalyst. The catalyst was prepared by dissolving a mixture of 2 grams (0.011 mols) of anhydrous zinc acetate and 4.45 grams (0.022 mols) of aluminum isopropoxide in 100 ml tetralin, and heating the resulting solution at 200° C. for 18 hours. After cooling to 25° C. the solvent was removed by evaporation under vacuum to produce 4.3 grams of a beige powder.

The active-hydrogen reactant for the alkoxylation was a NEODOL 23 Alcohol (trademark of and sold by Shell Chemical Company), characterized as a mixture of primary, 80% linear (20% branched), aliphatic alcohols containing twelve and thirteen carbon atoms (about 45% $C_{12}$, 55% $C_{13}$) Initially, the liquid alcohol reactant was dried by heating under a nitrogen sparge at 130° C. for one hour. Then, one gram (0.0026 mols) of the zinc and aluminum bimetallic oxo catalyst prepared as described above was added to the alcohol at 130° C. and the mixture was maintained at that temperature and under nitrogen sparge for an additional hour.

The catalyst and alcohol mixture was transferred to an autoclave reactor which was then sealed, heated to 170° C. and pressured to 70 psig with a mixture of ethylene oxide in nitrogen (40% ethylene oxide by mol). The reaction commenced without an induction period. Temperature in the autoclave was maintained at 170° C. and ethylene oxide was added to the reactor system, upon demand, to maintain the 70 psig pressure. About 45 grams of ethylene oxide reacted over a three hour period. The reactor was then maintained at 170° C. for an additional 30 minutes without further addition of ethylene oxide, to consume unreacted ethylene oxide in the system. The product was analyzed by combined GC/LC and found to have an average ethylene oxide adduct number (mols ethylene oxide reacted, divided by total mols of alcohol) of 1.5 and to contain 1.3%w polyethylene glycols (PEG). The distribution of the various adducts in the alkoxylate product of this Example is presented in the Table below and illustrated by Curve C in the attached drawing.

EXAMPLE 2

The procedures of Example 1 were repeated for the preparation of a product having an average ethylene oxide adduct number of 3.0. The product contained 1.2%w PEG.

COMPARATIVE EXPERIMENTS

Two comparative experiments illustrate that results of the use of a bimetallic catalyst according to the invention are distinguishable from results of the independent use as catalyst of compounds of the individual metals from which the bimetallic combination had been derived.

For one comparative experiment, 66 grams (0.340 mol) of NEODOL 23 Alcohol were dried at 130° C. for one hour under nitrogen sparge. One gram (0.0049 mol) of aluminum isopropoxide was added to the alcohol and the mixture then heated at 130° C. for one additional hour under nitrogen sparge. The catalyst and alcohol mixture was transferred to an autoclave, heated to 170° C. and pressurized to 70 psig with the ethylene oxide and nitrogen mixture. Temperature was maintained at 170° C. and ethylene oxide was added upon demand. After 5 hours, only 12 grams of EO had been consumed, resulting in a product mixture having an average ethylene oxide adduct number of only 0.73 and containing 0.3%w PEG.

For the second comparative experiment, the same procedures were carried out utilizing 50 grams (0.258 mol) of alcohol and one gram (0.0055 mol) of zinc acetate. After 4 hours reaction in the autoclave, only 2 grams of ethylene oxide had reacted. The product mixture contained too little alkoxylate for proper analysis.

EXAMPLE 3

An alkoxylation process in accordance with the invention was carried out using a bimetallic (cobalt and aluminum) oxo alkoxide catalyst. The catalyst was prepared by reacting cobalt acetate with aluminum isopropoxide (in a molar ratio of 2:1) under the procedures for catalyst preparation described in Example 1.

One gram (0.0026 mol) of the catalyst was mixed with 50 grams (0.258 mol) of NEODOL 23 Alcohol which had been dried at 130° C. for one hour under a nitrogen sparge, and the mixture was heated at 140° C. for one additional hour.

The catalyst and alcohol mixture was then transferred to the autoclave reactor, which was heated to 170° C. and pressured to 70 psig with the mixture of ethylene oxide (40% mol) in nitrogen. Alkoxylation commenced and ethylene oxide was added upon demand. After four hours, 30.8 grams of ethylene oxide had been added, producing an ethoxylate product mixture having an average adduct number of 2.8.

COMPARATIVE EXPERIMENTS

Experiments were also conducted under comparable procedures and conditions, but utilizing conventional catalysts and thus not in accordance with the invention. In one experiment, a potassium hydroxide catalyst was used to prepare an ethoxylate of the NEODOL 23 Alcohol reactant, having an average ethylene oxide adduct number of about 1.9. The adduct distribution is presented in the following Table and also indicated by curve A in the attached drawing.

In another experiment, a barium hydroxide catalyst and the same reactants were used to prepare a product having an average adduct number of about 1.7. The distribution is shown in the Table and by curve B of the drawing.

EXAMPLE 4

An alkoxylation process in accordance with the invention was practiced using a bimetallic (zinc and aluminum) catalyst supported on a silica carrier. The carrier was a Davison 57 silica (30–100 mesh) which had been dried at 300° C. under full vacuum for 18 hours. For preparation of the supported catalyst, one gram of a zinc/aluminum bimetallic oxo compound, prepared as described in Example 1, was dissolved in 50 grams of dry xylene and the solution added to 10 grams of the silica. The mixture was slurried at 85° C. for one hour. The solids were filtered, washed several times with xylene and dried under vacuum at 80° C. for one hour, to obtain a pale yellow powder.

For alkoxylation, three grams of the supported catalyst powder were added to 50 grams of active-hydrogen reactant (NEODOL 23 Alcohol). The process was carried out using conditions and procedures described in Example 1. A total of twenty-five grams of ethylene oxide reacted with the alcohol over a four-hour period to produce an ethoxylate mixture having an average adduct number of 1.5. Distribution of the several adducts was essentially the same as that of the product of Example 1.

TABLE

| Adduct Number p | CATALYST | | |
|---|---|---|---|
| | $Zn^{+2}/Al^{+3}$ bimetallic oxo catalyst | $K^+$ | $Ba^{+2}$ |
| 0 (unreacted alcohol) | 21.9% w | 28.9% w | 29.5% w |
| 1 | 24.9 | 13.1 | 12.9 |
| 2 | 24.5 | 13.2 | 15.8 |
| 3 | 15.8 | 11.5 | 15.8 |
| 4 | 7.3 | 8.9 | 12.3 |
| 5 | 1.9 | 6.5 | 7.3 |
| 6 | 1.6 | 4.8 | 3.4 |
| 7 | 0.9 | 3.5 | 1.8 |
| 8 | 0.6 | 2.6 | 0.7 |
| 9 | 0.4 | 2.0 | 0.3 |
| 10 | 0.3 | 1.4 | 0.1 |
| 11 | 0.1 | 1.1 | |
| 12 | | 0.7 | |
| 13 | | 0.6 | |
| 14 | | 0.4 | |
| 15 | | 0.3 | |

I claim as my invention:

1. A process for the preparation of alkylene oxide adducts of acyclic aliphatic alcohols which comprises contacting and reacting an alkylene oxide reactant selected from the group consisting of $C_2$ to $C_4$ vicinal alkylene oxides with one or more acyclic aliphatic alcohols in the presence of a catalytically effective amount of a bimetallic oxo compound of the formula $(RO)_n$—M—O—M'—O—M(OR)$_n$, wherein each R is a hydrocarbyl group, M' is a divalent metal selected from the group consisting of elements of Groups VIII, Ib, IIb, IIIb, and IVb of the Periodic Table, each M is a trivalent metal or a tetravalent metal, and each n is 2 if the adjacent M is a trivalent or 3 if the adjacent M is tetravalent, in a reaction zone having a liquid phase which comprises the said alcohols and is essentially free of added reaction solvent.

2. The process of claim 1, wherein M is a trivalent or tetravalent metal selected from the group consisting of aluminum, titanium, boron, vanadium, scandium, germanium, yttrium, zirconium, tin, lanthanum and other members of the lanthanide series, hafnium, tantalum, tungsten, palladium, and antimony.

3. The process of claim 2, wherein each M' is a divalent metal selected from the group consisting of cobalt, nickel, copper, zinc, rhodium, palladium, silver, cadmium, indium, tin, iridium, and platinum.

4. The process of claim 3, wherein each R is a $C_1$ to $C_{30}$ hydrocarbyl moiety.

5. The process of claim 4, wherein each R is an alkyl moiety, M' is selected from the group consisting of zinc, nickel and cobalt, and each M is selected from the group consisting of aluminum, titanium, boron and vanadium.

6. The process of claim 4, wherein each R is $C_1$ to $C_{20}$ alkyl moiety, M' is selected from the group consisting of zinc, nickel and cobalt, and each M is selected from the group consisting of aluminum, titanium, boron and vanadium.

7. The process of claim 6, wherein each R is a $C_1$ to $C_6$ alkyl moiety.

8. The process of claim 6, wherein the alkylene oxide reactant is selected from the group consisting of ethylene oxide, propylene oxide and mixtures thereof.

9. The process of claim 8, wherein the alcohols are $C_6$ to $C_{24}$ primary alcohols.

10. The process of claim 9, wherein the alcohols are $C_8$ to $C_{20}$ alcohols and the alkylene oxide reactant is ethylene oxide.

11. The process of claim 1, wherein the liquid phase in the reaction zone is solvent-free and consists essentially of the alcohol, the catalyst, and the alkylene oxide adduct product.

12. The process of claim 11, wherein the alkylene oxide reactant is ethylene oxide, the alcohols are $C_8$ to $C_{20}$ primary alcohols, each R is a $C_1$ to $C_{20}$ alkyl moiety, M' is selected from the group consisting of zinc, nickel and cobalt, and each M is selected from the group consisting of aluminum, titanium, boron, and vanadium.

13. The process of claim 1, wherein the bimetallic oxo compound is supported on a carrier.

14. The process of claim 12, wherein the bimetallic oxo compound is supported on a carrier.

15. A process for the preparation of ethylene oxide adducts of acyclic aliphatic primary alcohols which comprises contacting and reacting ethylene oxide with one or more $C_8$ to $C_{20}$ monohydric acyclic aliphatic primary alcohols in the presence of a catalytically effective amount of a bimetallic oxo compound of the formula $(RO)_nM$—O—M'—O—M(OR)$_n$, wherein each R is a $C_1$ to $C_{20}$ alkyl moiety, M' is a divalent metal selected from the group consisting of zinc, nickel and cobalt, each M is a trivalent or tetravlent metal selected from the group consisting of aluminum, titanium, boron and vanadium, and each n is 2 if the adjacent M is trivalent or 3 if the adjacent M is tetravalent, in a reaction zone which comprises (a) a gas phase containing the alkylene oxide reactant and (b) a liquid phase comprising the alcohols and essentially free of added reaction solvent.

16. The process of claim 15, wherein the liquid phase in the reaction zone consists essentially of the alcohol, the catalyst and the alkylene oxide adduct product.

17. The process of claim 16, wherein each R is a $C_1$ to $C_6$ alkyl moiety.

18. The process of claim 17, wherein the bimetallic oxo compound is supported on a carrier.

19. The process of claim 17, wherein the reaction zone comprises a liquid phase which is solvent-free and consists of the process reactants, catalyst and products.

* * * * *